(12) United States Patent
Berri

(10) Patent No.: US 11,744,928 B2
(45) Date of Patent: Sep. 5, 2023

(54) COLOSTRUM COLLECTION DEVICE

(71) Applicant: Maryam Berri, Dearborn, MI (US)

(72) Inventor: Maryam Berri, Dearborn, MI (US)

( * ) Notice: Subject to any disclaimer, the term of this patent is extended or adjusted under 35 U.S.C. 154(b) by 391 days.

(21) Appl. No.: 16/811,346

(22) Filed: Mar. 6, 2020

(65) Prior Publication Data
US 2020/0281816 A1    Sep. 10, 2020

Related U.S. Application Data

(60) Provisional application No. 62/814,491, filed on Mar. 6, 2019.

(51) Int. Cl.
| | | |
|---|---|---|
| *A61M 1/06* | (2006.01) | |
| *A61J 7/00* | (2006.01) | |
| *A61J 15/00* | (2006.01) | |
| *A61M 39/22* | (2006.01) | |
| *A61M 39/10* | (2006.01) | |
| *A61M 1/00* | (2006.01) | |

(52) U.S. Cl.
CPC .............. *A61M 1/06* (2013.01); *A61J 7/0053* (2013.01); *A61J 15/00* (2013.01); *A61M 1/066* (2014.02); *A61M 39/22* (2013.01); *A61M 1/815* (2021.05); *A61M 2039/1033* (2013.01)

(58) Field of Classification Search
CPC ...... A61J 7/0053; A61J 15/00; A61J 15/0011; A61J 1/20; A61J 11/00; A61J 11/0005; A61J 11/0035; A61J 11/005; A61J 7/0015; A61J 7/00; A61J 7/0038; A61M 1/06; A61M 1/066; A61M 1/067; A61M 1/069; A61M 1/0693; A61M 1/06935; A61M 1/0697; A61M 2039/1033; A61M 5/178; A61M 5/1782; A61M 1/062; A61M 1/068; A61M 39/10; A61M 39/22; A61M 2039/085; A61M 2210/1007; A61M 2202/0482; A47G 21/185
See application file for complete search history.

(56) References Cited

U.S. PATENT DOCUMENTS

| | | | | |
|---|---|---|---|---|
| 4,623,067 | A | | 11/1986 | Hejlik |
| 5,308,331 | A | * | 5/1994 | Avila .................. A61M 5/5066 604/218 |
| 9,248,077 | B1 | * | 2/2016 | Kelly ..................... A61M 1/062 |
| 9,566,387 | B2 | * | 2/2017 | Verhoeven ........ A61M 5/31526 |
| 9,642,952 | B1 | * | 5/2017 | Kelly ...................... A61M 1/06 |
| 2009/0227943 | A1 | * | 9/2009 | Schultz ................ A61J 7/0023 604/77 |

(Continued)

*Primary Examiner* — Emily L Schmidt
*Assistant Examiner* — Alexandra Lalonde
(74) *Attorney, Agent, or Firm* — DICKINSON WRIGHT PLLC

(57) ABSTRACT

A syringe receptacle device for collecting a liquid from an extraction device, a cylindrical barrel, and a plunger. The barrel has an inner circumferential surface that extends between opposite first and second ends. The first end of the barrel is adapted to be removably coupled to the extraction device. The plunger is slidably coupled to the barrel and includes a plunger head and an actuating rod. The plunger head is frictionally engaged with the inner circumferential surface of the barrel. The actuating rod is fixedly attached to the plunger head and extends out through the second end of the barrel.

14 Claims, 3 Drawing Sheets

(56) References Cited

U.S. PATENT DOCUMENTS

| | | | |
|---|---|---|---|
| 2014/0051926 A1* | 2/2014 | Oates, II | A61J 7/0053 |
| | | | 128/202.16 |
| 2015/0057608 A1* | 2/2015 | Hitscherich, Jr | A61M 5/3137 |
| | | | 604/218 |
| 2017/0095600 A1* | 4/2017 | Sherman | A61M 39/105 |
| 2017/0312181 A1* | 11/2017 | Davis | A61M 39/10 |
| 2018/0014998 A1* | 1/2018 | Yuki | A61J 15/0026 |

* cited by examiner

COLOSTRUM COLLECTION DEVICE

CROSS-REFERENCE TO RELATED APPLICATIONS

This application claims priority to and all the benefits of U.S. Provisional Patent Application No. 62/814,491, filed Mar. 6, 2019, entitled "Colostrum Collection Device," the disclosure of which is hereby incorporated by reference in its entirety.

BACKGROUND OF THE INVENTION

1. Field of the Invention

The present invention relates to a receptacle attachment for a breast pump machine capable of collecting and dispensing the extracted liquids, more particularly, extracted liquids such as colostrum, which is the first secretion from the mammary glands of a woman after giving birth.

2. Description of Related Art

Breast milk is uniquely adapted to the nutritional requirements of an infant and is distinctly superior to any substitute which has been devised by nutritional scientists. Breast milk, and more particularly, colostrum has been found to contribute directly to the infant's immunological adaptation to life after birth. Colostrum is a thicker and more viscous fluid than milk and can only be collected either a few days before or a few days after parturition and subsequently fed to an infant.

Extraction devices, such as breast pumps, are well known and are generally used to collect breast milk, colostrum, and other such fluids from the mammary glands of the mother's breast. Most breast pumps are generally comprised of a hood that fits over the breast, a vacuum pump connected to the hood for generating an intermittent vacuum (or negative pressure) within the hood, and a receptacle for collecting the expressed fluids. Breast pump receptacles are typically cylindrical in shape and simply collect the expressed milk to later be transferred to another container for feeding or storage. With colostrum, many doctors suggest using a syringe to suction the fluid from the receptacle to feed to the infant. A syringe is often used because many infants have trouble swallowing the colostrum due to its viscosity as well the general issues many infants have with suckling early on. The benefits of colostrum are immeasurable thus it is extremely important for an infant to receive as much of it as possible. Accordingly, it is desirable to have a single receptacle device that can be used to effectively feed, collect, and store the colostrum produced by the mother.

SUMMARY OF THE INVENTION

According to one embodiment, there is provided a syringe receptacle device for collecting a liquid from an extraction device, a cylindrical barrel, and a plunger. The barrel has an inner circumferential surface that extends between opposite first and second ends. The first end of the barrel is adapted to be removably coupled to the extraction device. The plunger is slidably coupled to the barrel and includes a plunger head and an actuating rod. The plunger head is frictionally engaged with the inner circumferential surface of the barrel. The actuating rod is fixedly attached to the plunger head an extends out through the second of the barrel.

BRIEF DESCRIPTION OF THE DRAWINGS

Advantages of the present disclosure will be readily appreciated as the same becomes better understood by reference to the following detailed description when considered in connection with the accompanying drawings wherein.

DETAILED DESCRIPTION OF THE EMBODIMENTS

FIGS. 2-8 illustrate a syringe receptacle device 10 configured to be removably attached to any conventional breast pump machine to collect and dispense fluids such as breast milk and/or colostrum. Directional references employed or shown in the description, figures, or claims, such as top, bottom, front, back, upper, lower, upward, downward, lengthwise, widthwise, left, right, and the like, are relative terms employed for ease of description and are not intended to limit the scope of the invention in any respect.

Figure 1:
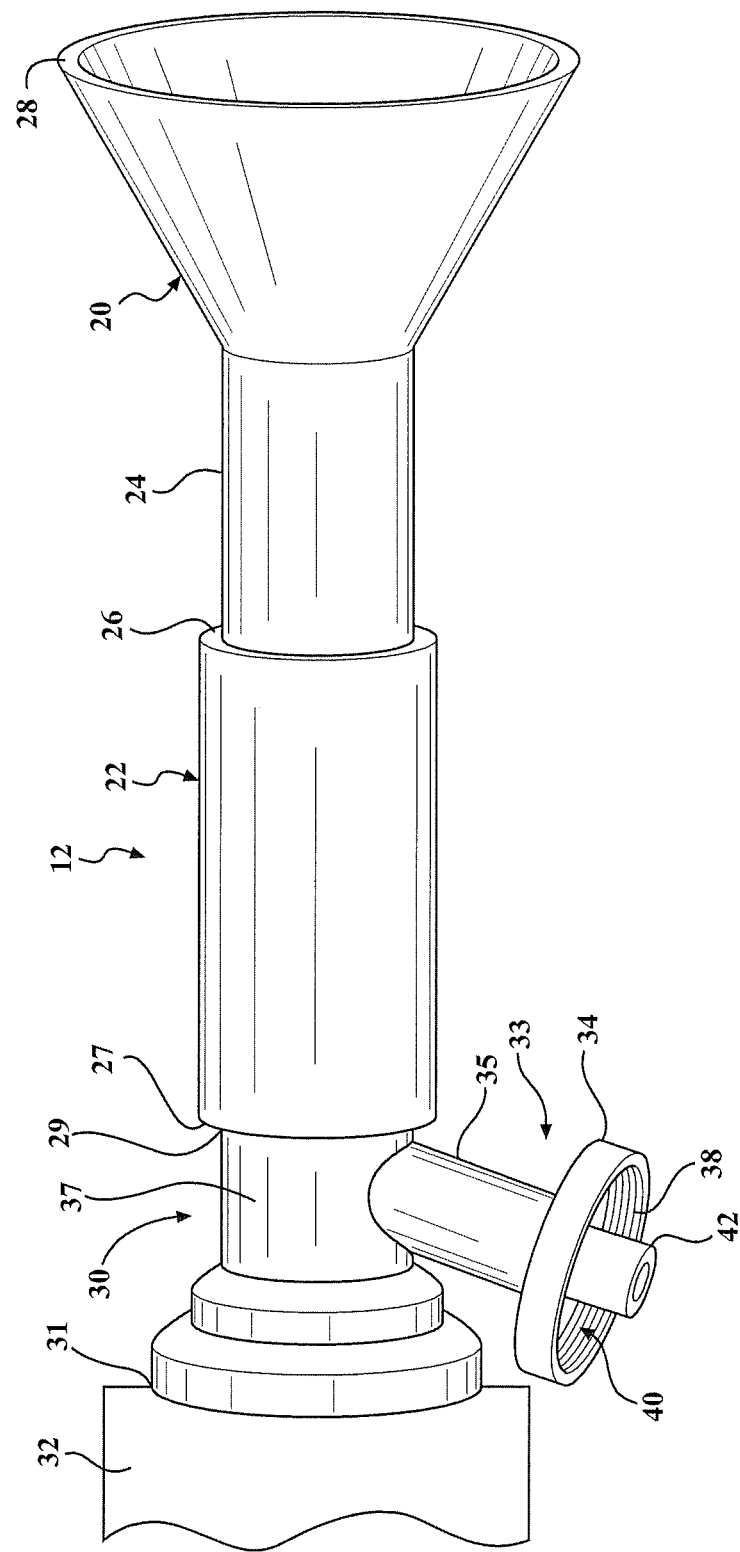
FIG. 1 is a perspective view of a conventional extraction device.
Figure 2:
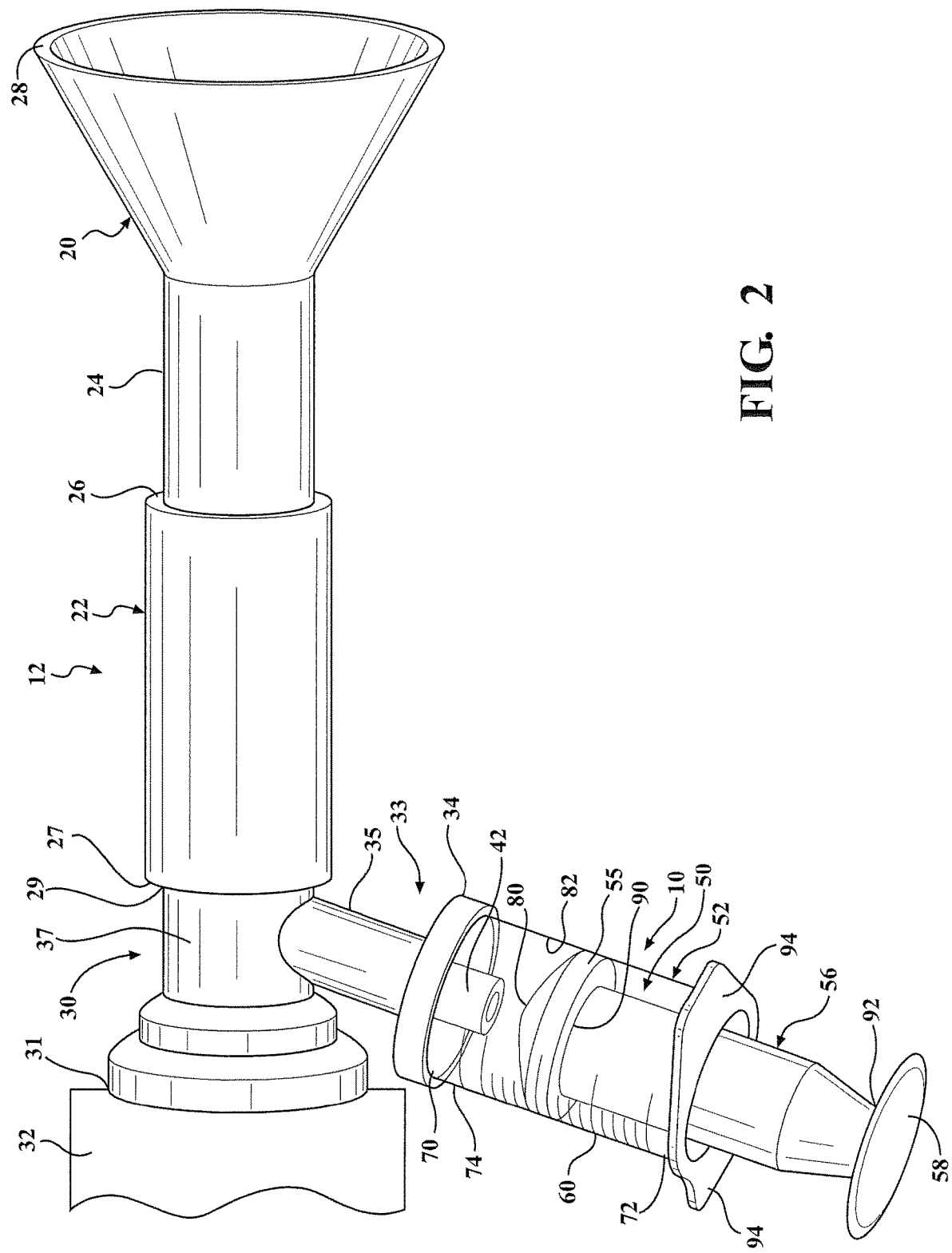
FIG. 2 is a perspective view of a syringe receptacle device according to one embodiment of the present invention attached to the conventional extraction device of FIG. 1.

FIGS. 1 and 2 illustrate one embodiment of a conventional breast pump machine or extraction device 12. The extraction device 12 includes a funnel 20, a breast pump connector 22, a suction device connector 30, and a source of suction 32. The funnel 20 includes a narrow end 24 and a wide end 28 opposite the narrow end 24. The breast pump connector 22 is a hollow cylindrical tube extending between an open front end 26 and an open back end 27. The funnel 20 may be removably attached to the breast pump connector 22 by inserting the narrow end 24 of the funnel 20 into the front end 26 of the breast pump connector 22.

The suction device connector 30 includes a main body 37 extending between a front end 29 and an opposite back end 31. The suction device connector 30 may be removably attached to the breast pump connector 22 by inserting the front end 29 of the suction device connector 30 into the back end 27 of the breast pump connector 22. The back end 31 of the suction device connector 30 and the source of suction 32 may include threading to removably couple the source of suction 32 to suction device connector 30.

The suction device connector 30 also includes a collection device connector 33 extending downwardly from the main body 37. The collection device connector 33 includes a receiving member 34, an arm member 35 and a one-way valve 42. The receiving member 34 includes internal threading 38 on an internal circumferential surface 40 to threadedly couple with a receptacle device, such as a baby bottle. The arm member 35 extends between the main body 37 of the suction device connector 30 and the receiving member 34. The one-way valve 42 extends from and is attached to the arm member 35 at the receiving member 34.

Figure 3:
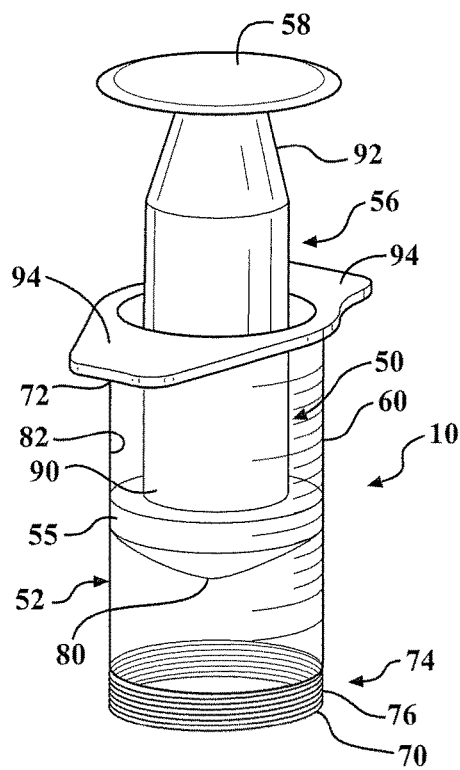
FIG. 3 is a perspective view of a syringe receptacle device according to one embodiment of the present invention.

Referring to FIGS. 2 and 3, the syringe receptacle device 10 includes a barrel 52 and a plunger 50 slidably coupled to the barrel 52. The barrel 52 extends between a first end 70 and a second end 72, and includes an inner circumferential surface 82 and an outer circumferential surface 74. The barrel 52 is preferably made from plastic. The first end 70 of the barrel 52 includes external threading 76 on the outer circumferential surface 74. The barrel 52 may further include indicia 60 to indicate the volumetric amount of contents in the syringe receptacle device 10. The barrel 52 also may include an extension member 94 extending transversely from the second end 72 of the barrel 52. The extension member 94 may be made from the same material as the barrel 52 and may vary in number, size, and shape from one embodiment to another.

The plunger 50 includes a plunger head 55 and an actuating rod 56. The plunger head 55 preferably has a conical shape with a central apex 80. Alternatively, the plunger head 55 may have a flat spherical shape. The actuating rod 56 may be cylindrically shaped and extends from a first end 90 to a second end 92. The first end 90 of the actuating rod 56 is fixedly attached to the plunger head 55.

The plunger 50 also may further include a plunger base 58 transversely extending from the second end 90 of the actuating rod 56. Although the plunger base 58 is depicted as circular in shape, the shape of the plunger base 58 may vary in other embodiments. The plunger base 58 preferably extends beyond the outer circumferential surface 74 of the barrel 52. The plunger base 58 creates a stable platform to hold the syringe receptacle device 10 upright when it is placed on a flat surface. A gripping material may be attached to the plunger base 58 to give it a more stable nonslip grip.

When the plunger 50 is inserted into the second end 72 of the barrel 52, the plunger 50 is capable of axial telescopic movement within the barrel 52. The second end 92 of the actuating rod 56 extends out from the second end 72 of the barrel 52, and the plunger base 58 prevents a user from fully inserting the actuating rod 56 into the barrel 52. The plunger head 55 frictionally engages the inner circumferential surface 82 of the barrel 52. The plunger head 55 may be made from a polyisoprene material to increase the frictional engagement between the plunger head 55 and the inner circumferential surface 82 of the barrel 52. Alternatively, the plunger head 55 may be made from the same plastic material as the barrel 52 to allow for smooth telescopic movement within the barrel 52 and provide cost savings during manufacturing.

Referring to FIGS. 4-8, the syringe receptacle device also includes a cap attachment 54 configured to be removably attached to the first end 70 of the barrel 52. Each cap attachment 54 includes a rim portion 100 and a face 120. The rim portion 100 is cylindrical in shape and extends between a first end 102 and a second end 104. The rim portion 100 includes internal threading 106 on an inner circumferential surface 108 of the rim portion 100. The face 120 is fixedly attached to the first end 102 of the cap attachment 54. The cap attachment 54 also includes a sealing ring 110 fixedly attached to the face 120 along the inner circumferential surface 108 of the rim portion 100. The sealing ring 110 is preferably made from a silicone or rubber-like material. FIGS. 4-8 illustrate a variety of cap attachments 54 with different faces 120.

Figure 4:
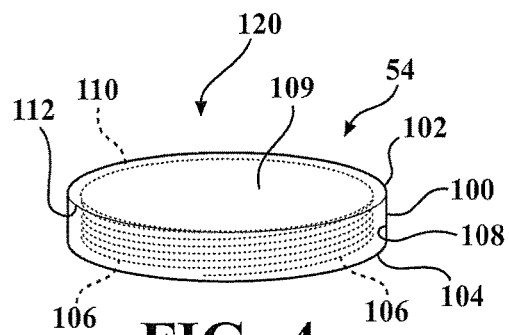
FIG. 4 is a partially transparent perspective view of a cap attachment according to one embodiment of the present invention.

FIG. 4 illustrates a first embodiment of the cap attachment 54. The face 120 of the cap attachment 54 comprises a disc 109 that completely encloses the first end 102 of the cap attachment 54 to seal fluids in the syringe receptacle device 10 for storage purposes.

Figure 5:
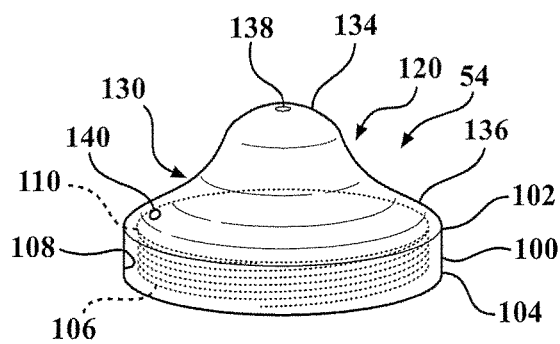
FIG. 5 is a partially transparent perspective view of a cap attachment according to a second embodiment of the present invention.

FIG. 5 illustrates a second embodiment of the cap attachment 54 where the face 120 comprises a flexible elastomeric nipple 130. The elastomeric nipple 130 includes a base end 136 and a tip end 134. The tip end 134 has a sealed opening 138 that opens in response to a sucking action on the nipple 130 to enable the flow of liquid from the barrel 52 through the nipple 130 to the infant's mouth. In some embodiments, the base end 136 may include an air inlet 140 which acts as a one-way valve to allow air to flow back into the barrel 52 to offset the negative pressure created in the barrel 52 due to the sucking action. The cap attachment 54 in FIG. 5 allows the infant to suck the liquid directly from the syringe receptacle device 10.

Figure 6:
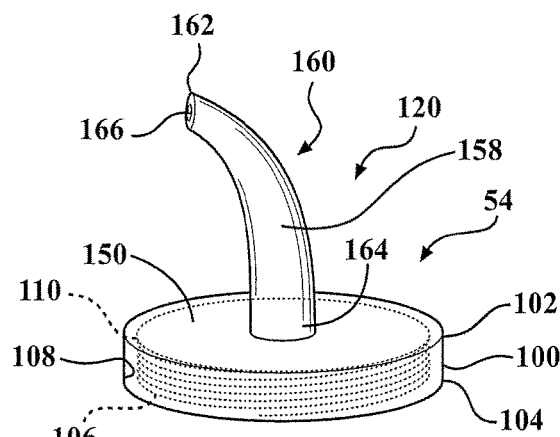
FIG. 6 is a partially transparent perspective view of a cap attachment according to a third embodiment of the present invention.

FIG. 6 illustrates a third embodiment of the cap attachment 54 where the face 120 includes a base portion 150 and an irrigation member 160 extending from the base portion 150. The irrigation member 160 includes a hollow curved frustoconical portion 158 extending from a first end 162 to a second end 164. The second end 164 is fixedly attached to the base portion 150 of the cap attachment 54. The first end 162 has a small opening 166. The cap attachment 54 in FIG. 6 is used in instances where the infant is having trouble swallowing large amounts of liquid quickly. The curved shape places the liquid in the back corner of the infant's mouth rather than directly down the center. Placing the liquid in the back corner allows the liquid to slowly move to the back of the infant's throat giving them more time to properly swallow.

Figure 7:
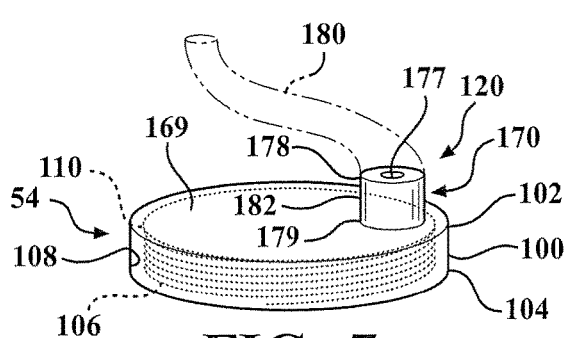
FIG. 7 a partially transparent perspective view of a cap attachment according to a fourth embodiment of the present invention.

FIG. 7 illustrates a fourth embodiment of the cap attachment 54 where the face 120 includes a base portion 169 and a cylindrical member 170 extending from the base portion 169. The cylindrical member 170 includes a central opening 177 extending from a first end 178 to a second end 179. The second end 179 is fixedly attached to the base portion 169 of the cap attachment 54. A feeding tube 180 may be releasably secured around an outer circumferential surface 182 of the cylindrical member 170. The feeding tube 180 may be made of a flexible medical grade material that can be inserted into an infant's gastrointestinal tract for direct administration of the liquid from the barrel 52 into the infant.

Figure 8:
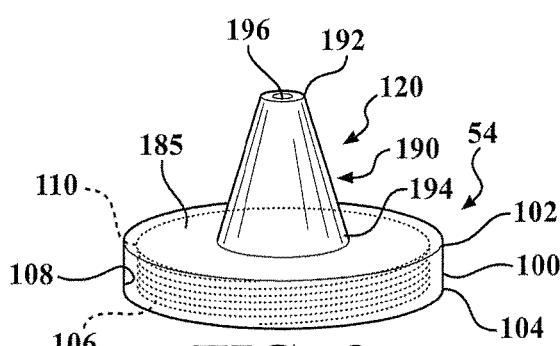
FIG. 8 a partially transparent perspective view of a cap attachment according to a fifth embodiment of the present invention.

FIG. 8 illustrates a fifth embodiment of the cap attachment 54 where the face 120 a base portion 185 and a cone shaped tip 190 extending from the base portion 185. The cone shaped tip 190 has a hollow interior extending from a first end 192 to a second end 194. The second end 194 is fixedly attached to the base portion 185 of the cap attachment 54. The first end 192 has a small opening 196. The cap attachment 54 in FIG. 8 may be used to insert fluid into the infant's mouth when the infant is unable to extract fluid from the nipple attachment 54 depicted in FIG. 5.

To set up the device, the syringe receptacle device 10 is attached to the receiving member 34, and the plunger 50 is retracted to allow maximum space within the barrel 52. Breast milk and/or colostrum may be expressed into the wide end 28 of the funnel 20. Suction applied through the breast pump connector 22 via the suction source 32 draws the colostrum from the breast through the collection device connector 33 and into the syringe receptacle device 10. When the pumping process is complete and the milk and colostrum are captured in the barrel 52, the syringe receptacle device 10 is disconnected from the extraction device 12. The cap attachment 54 of the user's choice may then be threadedly coupled to the first end 70 of the barrel 52 for the purpose of storing or feeding the liquids to an infant, as discussed above. During the feeding process, the plunger 50 may be depressed into the barrel 52 to assist an infant having trouble suckling or to ensure the infant has received the total contents of the syringe receptacle device 10.

The variety of cap attachments 54 seen in FIGS. 4-8 allows for a variety of feeding and storage methods depending on the user's desires or needs. The advantage of using the syringe receptacle device 10 to collect the expressed fluids is that no other containers or receptacles are needed for the feeding. By attaching the cap attachment 54 and depressing the plunger 50 into the barrel 52 the total contents of the barrel 52 can be delivered to the infant. Furthermore, the syringe receptacle device 10 can help feed infants who may have trouble sucking early on in life. The ability to deliver the full contents of the barrel 52 becomes significantly more important when dealing with colostrum which is very important to an infant's development and relatively limited in quantity.

The invention has been described in an illustrative manner, and it is to be understood that the terminology, which has been used, is intended to be in the nature of words of description rather than of limitation. Many modifications and variations of the present invention are possible in light of the above teachings. It is, therefore, to be understood that within the scope of the appended claims, the invention may be practiced other than as specifically described.

The invention claimed is:

1. A system comprising an extraction device and a syringe receptacle device for collecting a liquid from the extraction device, the syringe receptacle device comprising:
   a cylindrical barrel having an inner circumferential surface extending between opposite first and second ends, wherein the first end of the barrel includes an external threading that is adapted to be removably coupled to the extraction device;
   a cap attachment adapted to be removably coupled to the first end of the barrel, the cap attachment comprises:
      a cylindrical rim extending between a first end and a second end, the cylindrical rim includes an internal threading to couple the cap attachment with the external threading on the barrel; and
      a face extending across the first end of the cylindrical rim, the face comprises a flexible elastomeric nipple including a tip end, a sealed opening at the tip end adapted to be opened in response to a sucking action on the sealed opening, a base end coupled to the cylindrical rim, and an air inlet at the base end between the sealed opening and the first end of the cylindrical rim, the air inlet is offset from a longitudinal axis extending through the sealed opening and each of the first end and the second end of the barrel, the air inlet allowing air to flow through the air inlet when liquid flows through the sealed opening, and
   a plunger slidably coupled to the barrel, wherein the plunger comprises:
      a plunger head frictionally engaging the inner circumferential surface of the barrel; and
      an actuating rod fixedly attached to the plunger head, wherein the actuating rod extends through the second end of the barrel, and the extraction device comprises:
   a suction device connector, the suction device connector removably coupleable to a source of suction;
   a breast pump connector coupled to the suction device connector; and
   a collection device connector extending from the suction device connector and including internal threading for threadably coupling to the external threading of the barrel.

2. The system of claim 1 wherein the cap attachment seals the first end of the barrel when the cap attachment is coupled to the barrel.

3. The system of claim 1 wherein the syringe receptacle device further comprises a second cap attachment with a face comprising a base structure extending along a first end of a rim and a feeding structure extending from the base structure away from the rim.

4. The system of claim 3 wherein the feeding structure comprises an irrigation member having a curved frustoconical shape.

5. The system of claim 3, wherein the syringe receptacle device further comprises a feeding tube having a first end adapted to be releasably attached to the feeding structure and a second end adapted to be inserted into a gastrointestinal tract.

6. The system of claim 3 wherein the feeding structure comprises a cone-shaped tip extending from a first end having a first diameter to a second end having a second diameter wherein the first diameter is less than the second diameter and the second end of the cone-shaped tip is fixedly attached to the base structure.

7. The system of claim 1 wherein the actuating rod extends from a first end to a second end and the first end of the actuating rod is fixedly attached to the plunger head, wherein the plunger further comprises a plunger base transversely extending from the second end of the actuating rod.

8. The system of claim 7 wherein the plunger base is wider than the second end of the barrel.

9. The system of claim 7 wherein the plunger base is circular in shape.

10. The system of claim 7 wherein the plunger further comprises a gripping material attached to the plunger base on a side opposite the actuating rod.

11. The system of claim 1 wherein the barrel includes an extension transversely extending from the second end of the barrel away from the inner circumferential surface.

12. A syringe receptacle device for collecting a liquid from an extraction device, the syringe receptacle device comprising:
   a cylindrical barrel having an inner circumferential surface extending between opposite first and second ends, wherein the first end of the barrel includes an external threading to be adapted to be removably coupled to the extraction device;
   a plunger slidably coupled to the barrel, wherein the plunger comprises:
      a plunger head frictionally engaging the inner circumferential surface of the barrel; and
      an actuating rod fixedly attached to the plunger head, wherein the actuating rod extends through the second end of the barrel;
   a cap attachment adapted to be removably coupled to the first end of the barrel, the cap attachment comprises:
      a cylindrical rim extending between a first end and a second end, the cylindrical rim includes an internal threading to couple the cap attachment with the external threading on the barrel; and a face extending across the first end of the cylindrical rim, the face comprises a flexible elastomeric nipple including a tip end, a sealed opening at the tip end adapted to be opened in response to a sucking action on the sealed opening, a base end coupled to the cylindrical rim, and an air inlet at the base end between the sealed opening and the first end of the cylindrical rim, the air inlet is offset from a longitudinal axis extending through the sealed opening and each of the first end and the second end of the barrel, the air inlet allowing air to flow through the air inlet when liquid flows through the sealed opening.

13. The syringe receptacle device of claim 12, wherein the actuating rod extends from a first end to a second end and the first end of the actuating rod is fixedly attached to the plunger head, wherein the plunger further comprises a plunger base transversely extending from the second end of the actuating rod, the plunger base is wider than the second end of the barrel and circular in shape, the plunger further comprises a gripping material attached to the plunger base on a side opposite the actuating rod.

14. The syringe receptacle device of claim 12, wherein the barrel includes an extension transversely extending from the second end of the barrel away from the inner circumferential surface.

* * * * *